United States Patent [19]

Montavon et al.

[11] 4,178,443

[45] Dec. 11, 1979

[54] DERIVATIVES OF 7 [-SUBSTITUTED OXYIMINS ACETAMIDO] CEPHALOSPORINS

[75] Inventors: Marc Montavon; Roland Reiner, both of Basel, Switzerland

[73] Assignee: Hoffmann-La Roche Inc., Nutley, N.J.

[21] Appl. No.: 908,708

[22] Filed: May 23, 1978

[30] Foreign Application Priority Data

Jun. 3, 1977 [LU] Luxembourg ............................ 77485

[51] Int. Cl.² .......................................... C07D 501/36
[52] U.S. Cl. ...................................... 544/27; 544/26; 424/246
[58] Field of Search ..................................... 544/26, 27

[56] References Cited

U.S. PATENT DOCUMENTS 3,971,778   7/1976   Cook et al. ............................. 544/27

FOREIGN PATENT DOCUMENTS 831787   1/1976   Belgium .

Primary Examiner—David Wheeler
Attorney, Agent, or Firm—Jon S. Saxe; Bernard S. Leon; Frank P. Hoffman

[57] ABSTRACT

The acyl derivatives provided by the present invention are compounds of the general formula wherein R represents furyl, thienyl or phenyl optionally substituted by halogen, hydroxy, lower alkoxy or lower alkyl, $R_1$ represents alkyl or aminocarbonylmethyl and X represents a group of the formula in which one of the two symbols $R_2$ and $R_3$ or $R_4$ and $R_5$ represents hydrogen
and the other represents lower alkyl, carboxymethyl or sulphomethyl, and the pharmaceutically acceptable salts of said compounds and hydrates of said salts.

Also disclosed are a process for the manufacture of the compounds and pharmaceutical preparations therefor.

The compounds of the present invention have antibiotic activity, especially bactericidal activity.

7 Claims, No Drawings

DERIVATIVES OF 7 [-SUBSTITUTED OXYIMINS ACETAMIDO] CEPHALOSPORINS

DESCRIPTION OF THE INVENTION

The present invention relates to acyl derivatives. More particularly, the invention is concerned with acyl derivatives, a process for the manufacture thereof and pharmaceutical preparations containing same.

The acyl derivatives provided by the present invention are compounds of the general formula

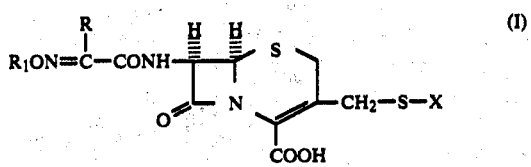

, wherein R represents furyl, thienyl or phenyl optionally substituted by halogen, hydroxy, lower alkoxy or lower alkyl, $R_1$ represents alkyl or aminocarbonylmethyl and X represents a group of the formula

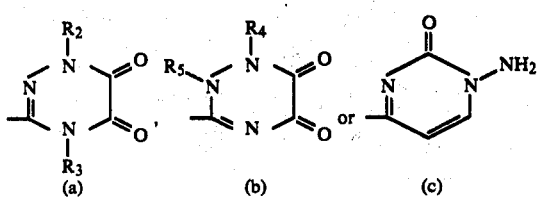

in which one of the two symbols $R_2$ and $R_3$ or $R_4$ and $R_5$ represents hydrogen and the other represents lower alkyl, carboxymethyl or sulphomethyl, as well as salts of said compounds and hydrates of said salts.

Examples of salts of the compounds of formula I are alkali metal salts such as the sodium and potassium salt, the ammonium salt, alkaline earth metal salts such as the calcium salt, salts with organic bases such as salts with amines (e.g. salts with N-ethyl-piperidine, procaine, dibenzylamine, N,N'-dibenzylethylethylenediamine, alkylamines or dialkylamines) as well as salts with amino acids (e.g. salts with arginine or lysine). The salts can be mono-salts or di-salts. The second salt formation occurs at the tautomeric enol form of the triazine group (b), said form being acidic.

The compounds of formula I also form acid addition salts with organic or inorganic acids. Examples of such salts are hydrohalides (e.g. hydrochlorides, hydrobromides and hydroiodides) as well as other mineral acid salts (e.g. sulphates, nitrates, phosphates and the like), alkylsulphonates and monoarylsulphonates (e.g. ethanesulphonates, toluenesulphonates, benzenesulphonates and the like) and other organic acid salts (e.g. acetates, tartrates, maleates, citrates, benzoates, salicylates, ascorbates and the like).

The salts of the compounds of formula I can be hydrated. The hydration can be effected in the course of the manufacturing process or can occur gradually as a consequence of the hygroscopic properties of an initially anhydrous salt of a compound of formula I.

The aforementioned lower alkyl groups are either straight-chain or branched-chain and can contain up to 7 carbon atoms (e.g. methyl, ethyl, n-propyl, isopropyl, n-pentyl and n-heptyl). The lower alkoxy groups have an analogous significance. The halogen atom is fluorine, chlorine, bromine or iodine with chlorine and bromine being preferred.

Preferred groups denoted by R are furyl, thienyl and phenyl, especially furyl. $R_1$ preferably represents methyl. X preferably represents the group of formula (c) or a group of formula (a) or (b) in which one of the two symbols $R_2$ and $R_3$ or $R_4$ and $R_5$ represents hydrogen and the other represents methyl. Especially preferred groups denoted by X are the 1,2,5,6-tetrahydro-2-methyl-5,6-dioxo-as-triazin-3-yl group and the 1,4,5,6-tetrahydro-4-methyl-5,6-dioxo-as-triazin-3-yl group.

Preferred acyl derivatives provided by the present invention are the compound (R)-7-[2-(2-furyl)-2-(methoxyimino)-acetamido]-3-[[(1,2,5,6-tetrahydro-2-methyl-5,6-dioxo-as-triazin-3-yl) thio]methyl]-3-cephem-4-carboxylic acid and salts thereof as well as the hydrates of said salts.

The compounds of formula I as well as their salts and hydrates of said salts can exist in the syn-isomeric form

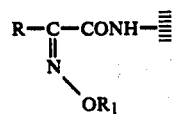

or in the anti-isomeric form

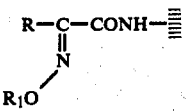

or as mixtures of these two forms. The syn-isomeric form is preferred as are mixtures in which the syn-isomeric form predominates.

According to the process provided by the present invention the acyl derivatives aforesaid (i.e. the compounds of formula I as well as their salts and hydrates of said salts) are manufactured by (a) reacting a compound of the general formula

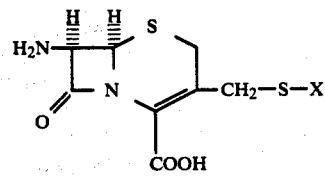

, wherein X has the significance given earlier and the carboxy group can be present in protected form, with an acid of the general formula

, wherein R and $R_1$ have the significance given earlier, or with a reactive functional derivative of this acid and, where required, cleaving off the protecting group, or (b) reacting a compound of the general formula

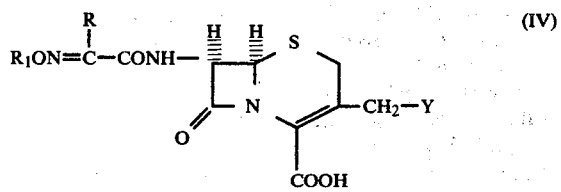

, wherein R and $R_1$ have the significance given earlier, Y represents a leaving group and the carboxy group can be present in protected form,
with a thiol of the general formula

HS—X                (V)

, wherein X has the significance given earlier, and, where required, cleaving off the protecting group, and (c) if desired, converting the reaction product into a salt or a hydrate of such a salt.

The carboxy groups present in the starting materials of formulae II and IV can be protected if desired; for example, by esterification to form a readily cleavable ester such as a silyl ester (e.g. the trimethylsilyl ester). The carboxy group can also be protected by salt formation with an inorganic base or a tertiary organic base such as triethylamine.

Examples of reactive functional derivatives of acids of formula III include halides (i.e. chlorides, bromides and fluorides), azides, anhydrides, especially mixed anhydrides with strong acids, reactive esters, (e.g. N-hydroxysuccinimide esters) and amides (e.g. imidazolides).

Examples of leaving groups denoted by Y in compounds of formula IV include halogen atoms (e.g. chlorine, bromine or iodine), acyloxy groups (e.g. lower alkanoyl groups such as acetoxy), lower alkylsulphonyloxy or arylsulphonyloxy groups (e.g. mesyloxy or tosyloxy) and the azido group.

The reaction of a compound of formula II with an acid of formula III or a reactive derivative thereof can be carried out in a manner known per se. Thus, for example, a free acid of formula III can be condensed with one of the aforementioned esters of a compound of formula II in the presence of a carbodiimide (e.g. dicyclohexylcarbodiimide) in an inert solvent (e.g. ethyl acetate, acetonitrile, dioxan, chloroform, methylene chloride, benzene or dimethylformamide) and the ester group can subsequently be cleaved off. Oxazolium salts (e.g. N-ethyl-5-phenyl-isoxazolium-3'-sulphonate) can be used in the place of carbodiimides.

According to another embodiment, a salt of an acid of formula II (e.g. a trialkylammonium salt) is reacted with a reactive functional derivative of an acid of formula III as mentioned earlier in an inert solvent (e.g. one of the solvents specified earlier).

According to a further embodiment, an acid halide, preferably the acid chloride, of an acid of formula III is reacted with an amine of formula II. The reaction is preferably carried out in the presence of an acid-binding agent; for example, in the presence of aqueous alkali, preferably sodium hydroxide, or in the presence of an alkali metal carbonate such as potassium carbonate, or in the presence of a lower-alkylated amine such as triethylamine. Water is preferably used as the solvent, although the reaction can also be carried out in an aprotic organic solvent such as, for example, dimethylformamide, dimethyl sulphoxide or hexamethylphosphoric acid triamide.

The reaction of a compound of formula II with a compound of formula III or a reactive functional derivative thereof can be carried out conveniently at a temperature between about −40° C. and room temperature, for example at about 0°–10° C.

The reaction of a compound of formula IV with a thiol of formula V can be carried out in a manner known per se; for example, at a temperature between about 40° C. and 80° C., conveniently at about 60° C., in a polar solvent such as an alcohol (e.g. a lower alkanol such as ethanol, propanol and the like), dimethylformamide or dimethyl sulphoxide, but preferably in water or in a buffer solution having a pH of about 6 to 7, preferably 6.5.

After completion of the reaction of a compound of formula II with an acid of formula III or a reactive derivative thereof or of the reaction of a compound of formula IV with a thiol of formula V, any protecting group present is cleaved off. Where the protecting group is a silyl group (silyl ester), this group can be cleaved off especially readily by treating the reaction product with water. Where the carboxyl group of an acid of formula IV is protected by salt formation (e.g. with triethylamine), then the cleavage of this salt-forming protecting group can be carried out by treatment with acid. In this case there can be used as the acid, for example, hydrochloric acid, sulphuric acid, phosphoric acid or citric acid.

The starting materials of formula II hereinbefore can be prepared by reacting a compound of the general formula

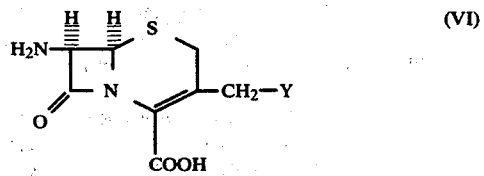

, wherein Y has the significance given earlier and the carboxy group can be present in protected form,
with a thiol of formula V hereinbefore. The reaction can be carried out under the same conditions as described earlier in connection with the reaction of a compound of formula IV with a thiol of formula V.

A syn/anti mixture of a compound of formula I which may be obtained can be separated into the corresponding syn- and anti-forms in the usual manner; for example, by recrystallisation or by chromatographic methods using a suitable solvent or solvent mixture.

The compounds of formula I, their salts and the hydrates of said salts have antibiotic, especially bactericidal, activity. They have a wide spectrum of activity against gram-positive and gram-negative microorganisms, including β-lactamase-producing staphylococci and various β-lactamase-producing gram-negative bacteria such as, for example, Haemophilus influenzae, Escherichia coli, Proteus species and Klebsiella species.

The compounds of formula I as well as their pharmaceuticall acceptable salts and hydrates of said salts can be used for the treatment and prophylaxis of infectious diseases. In the case of adults a daily dosage of about 1 g to about 4 g may be administered. Administration by the parenteral route is especially preferred.

In order to demonstrate the antimicrobial activity of the compounds provided by the present invention, the following representative compounds were tested:

Compound A: (7R)-7-[2-(2-furyl)-2-(methoxyimino)acetamido]-3-[[(1,2,5,6-tetrahydro-2-methyl-5,6-dioxo-as-triazin-3-yl)thio]methyl]-3-cephem-4-carboxylic acid.

Compound B: (7R)-7-[2-(2-furyl)-2-(methoxyimino)acetamido]-3-[[(1-amino-1,2-dihydro-2-oxo-4-pyrimidinyl)thio]-methyl]-3-cephem-4-carboxylic acid.

Compound C: (7R)-7-[2-(phenyl)-2-(methoxyimino)acetamido]-3-[[(1,2,5,6-tetrahydro-2-methyl-5,6-dioxo-as-triazin-3-yl)thio]methyl ]-3-cephem-4-carboxylic acid.

Compound D: (7R)-7-[2-(2-furyl)-2-(methoxyimino)acetamido]-3-[[(1,4,5,6-tetrahydro-4-methyl-5,6-dioxo-as-triazin-3-yl)thio]methyl]-3-cephem-4-carboxylic acid.

Compound E: (7R)-7-[2-methoxyimino)-2-(2-thienyl)acetamido]-3-[[(1,2,5,6-tetrahydro-2-methyl-5,6-dioxo-as-triazin-3-yl)thio]methyl]-3-cephem-4-carboxylic acid.

Compound F: (7R)-3-[[1-ethyl-1,4,5,6-tetrahydro-5,6-dioxo-as-triazin-3-yl)thio]methyl]-7-[2-(2-furyl)-2-(methoxyimino)acetamido]-3-cephem-4-carboxylic acid.

Compound G: (7R)-7-[2-[(carbamoylmethoxy)imino]-2-(2-furyl)-acetamido]-3-[[(1,4,5,6-tetrahydro-4-methyl-5,6-dioxo-as-triazin-3-yl)thio]methyl]-3-cephem-4-carboxylic acid.

pound are administered and the dosage at which 50% of the mice survice ($CD_{50}$, mg/kg) is determined by interpolation.

| Test compound | A | B | C | D | E | F | G |
|---|---|---|---|---|---|---|---|
| $CD_{50}$, mg/kg | 0.09 | 3.0 | 0.60 | 0.70 | 1.15 | 0.85 | 0.80 |

TOXICITY (mice, 24 hour values)

| Test compound | A | B | C | D | E | F | G |
|---|---|---|---|---|---|---|---|
| $LD_{50}$, mg/kg i.v. | 500–1000 | 1000–2000 | 1000–2000 | 500–1000 | 2000–4000 | 1000–2000 | >4000 |
| s.c. | >4000 | | | >4000 | | | |
| p.o. | >5000 | | | >5000 | | | |

Activity in vitro: Minimum Inhibitory Concentration (μg/ml)

| | | A | B | C | D | E | F | G |
|---|---|---|---|---|---|---|---|---|
| *Haemophilus influenzae* | strain 1 | 1.2 | 2.5 | 2.5 | 2.5 | 2.5 | 2.5 | 5.0 |
| | strain 2 | 0.16 | 0.63 | 0.16 | 0.31 | 0.16 | 0.31 | 0.63 |
| | strain 3 | 0.16 | 0.63 | 0.16 | 0.31 | 0.16 | 1.2 | 0.31 |
| | strain 4 | 0.16 | 0.31 | 0.16 | 0.31 | 0.16 | 0.16 | 0.63 |
| | strain 5 | 0.08 | 0.31 | 0.08 | 0.16 | 0.08 | 0.08 | 0.31 |
| | strain 6 | 0.16 | 0.31 | 0.08 | 0.16 | 0.08 | 0.08 | 0.63 |
| | strain 7 | 0.08 | 0.31 | 0.08 | 0.16 | 0.08 | 0.16 | 0.63 |
| *Klebsiella pneumoniae* | | 10 | 20 | 20 | 5 | 40 | 40 | 2.5 |
| *Escherichia coli* | | | | | | | | |
| | strain 1 | 0.63 | 2.5 | 1.2 | 0.16 | 2.5 | 1.2 | 0.31 |
| | strain 2 | 40 | 20 | 10 | 5 | 20 | 80 | 5 |
| *Proteus mirabilis* | | | | | | | | |
| | strain 1 | 2.5 | 10 | 10 | 10 | 10 | 20 | 5 |
| | strain 2 | 5 | 40 | 20 | 20 | 20 | 40 | 10 |
| *Proteus vulgaris* | | 5 | 40 | 10 | 1.2 | 10 | 20 | 1.2 |
| *Proteus rettgeri* | | 0.63 | 2.5 | 0.63 | 0.63 | 2.5 | 10 | 0.63 |
| *Staphylococcus aureus* ATCC 6538 | | 2.5 | 0.16 | 2.5 | 0.63 | 2.5 | 5 | 1.2 |
| Penicillin-resistant strain | | 5 | 1.2 | 2.5 | 0.63 | 2.5 | 5 | 1.2 |

ACTIVITY IN VIVO

Groups of 10 mice are infected intraperitoneally with an aqueous suspension of Proteus mirabilis. One hour after the infection the test compound is administered subcutaneously. The number of surviving mice is determined on the 4th day. Various dosages of test com- Pharmaceutical preparations, preferably dry ampoules, can contain the compounds of formula I, their pharmaceutically acceptable salts or hydrates of said salts, optionally in admixture with another therapeutically valuable substance. Such compounds, salts or hydrates are conveniently mixed with pharmaceutical inorganic or organic inert carrier material, especially one which is suitable for parenteral administration, such as, for example, water or gum arabic. The pharmaceutical preparations are preferably made up in liquid form (e.g. as solutions, suspensions or emulsions). The pharmaceutical preparations may be sterilised and/or may contain adjuvants such as preserving agents, stabilising agents, wetting agents, emulsifying agents, salts for varying the osmotic pressure or buffers.

The following Examples illustrate the process provided by the present invention:

EXAMPLE 1

Preparation of the sodium salt of (7R)-7-[2-furyl)-2-(methoxyimino)acetamido]-3-[[(1,2,5,6-tetrahydro-2-methyl-5,6-dioxo-as-triazin-3-yl)thio]methyl]-3-cephem-4-carboxylic acid 5.06 g of 2-methoxyimino-2-furyl-acetic acid (syn-/anti mixture 80:20) are dissolved in 150 ml of benzene and treated at 5°–10° C. while gassing with nitrogen with 4.2 ml of triethylamine, 2.6 ml of oxalyl chloride and 6 drops of dimethylformamide. The mixture is stirred while gassing with nitrogen at 5°–10° C. for 1 hour and at 25° C. for 0.5 hour and then evaporated at 40° C. in vacuo. The residue is suspended in 150 ml of acetone and treated at 0° C. with a solution of 11.2 g of (7R)-7-amino-3-desacetoxy-3-[(1,2,5,6-tetrahydro-2-methyl-5,6-dioxo-as-triazin-3-yl)thio]cephalosporanic acid in 150 ml of water, which has previously been adjusted to pH 7.5 using 2-N aqueous sodium hydroxide. The mixture is stirred at 0°–10° C. for 2.5 hours under nitrogen, the pH being held between 7.5 and 8.0 by the addition of 2-N aqueous sodium hydroxide. 500 ml of ethyl acetate are then added and the pH is adjusted to 1.5 with 2-N aqueous hydrochloric acid. After separating the organic phase, the aqueous phase is extracted once with ethyl acetate. The combined organic phases are washed twice with saturated aqueous sodium chloride solution, dried over sodium sulphate and concentrated to a volume of ca 100 ml. Insolubles are filtered off and the orange coloured filtrate obtained is diluted with 1000 ml of ether. The amorphous (7R)-7-[2-(2-furyl)-2-(methoxyimino)acetamido]-3-[[(1,2,5,6-tetrahydro-2-methyl-5,6-dioxo-as-triazin-3-yl)thio]methyl]-3-cephem-4-carboxylic acid which thereby precipitates is filtered off under suction and washed with ether and with low-boiling petroleum ether. The beige coloured product obtained is dissolved in 250 ml of ethyl acetate and insolubles are filtered off. The orange coloured filtrate is treated with 10 ml of a 2-N solution of sodium 2-ethylcaproate in ethyl acetate, whereby the sodium salt of (7R)-7-[2-(2-furyl)-2-(methoxyimino)acetamido]-3-[[(1,2,5,6-tetrahydro-2-methyl-5,6-dioxo-as-triazin-3-yl)thio]methyl]-3-cephem-4-carboxylic acid precipitates. This is filtered off under suction, washed with ethyl acetate and low-boiling petroleum ether and dried at 25° C. in vacuo for 2 days. The product obtained is a beige coloured powder (syn/anti mixture 80:20); $[\alpha]_D^{20} = -108.6°$ (c=0.5 in water); $R_f$ value=0.10 [thin-layer chromatography on Kieselgel-$F_{254}$-finished plates in butanol/glacial acetic acid/water (4:1:1), visualisation with ultraviolet light].

EXAMPLE 2

Preparation of the sodium salt of (7R)-7-[2-(2-furyl)-2-(methoxyimino)acetamido]-3-[[(1-amino-1,2-dihydro-2-oxo-4-pyrimidinyl)thio]methyl]-3-cephem-4-carboxylic acid This salt is prepared in a manner analogous to that described in Example 1 from 3.4 g of 2-methoxyimino-2-furyl-acetic acid and 7.11 g of (7R)-7-amino-3-desacetoxy-3-[(1-amino-1,2-dihydro-2-oxo-4-pyrimidinyl)thio]cephalosporanic acid. The product is a beige powder (syn/anti mixture 70:30); $R_f$ value=0.40 [thin-layer chromatography on Kieselgel-$F_{254}$-finished plates in butanol/glacial acetic acid/water (4:1:1), visualisation with ultraviolet light].

EXAMPLE 3

Preparation of the sodium salt of (7R)-7-[2-(phenyl)-2-(methoxyimino)acetamido]-3-[[(1,2,5,6-tetrahydro-2-methyl-5,6-dioxo-as-triazin-3-yl)thio]methyl]-3-cephem-4-carboxylic acid This salt is prepared in a manner analogous to that described in Example 1 from 1.8 g of 2-methoxyimino-phenyl-acetic acid (syn/anti mixture 90:10) and 3.75 g of (7R)-7-amino-3-desacetoxy-3-[(1,2,5,6-tetrahydro-2-methyl-5,6-dioxo-as-triazin-3-yl)thio]cephalosporanic acid. The product is a beige powder (syn/anti mixture 90:10); $[\alpha]_D^{20}=135°$ (c=0.5 in water); $R_f$ value=0.17 [thin-layer chromatography on Kieselgel-$F_{254}$-finished plates in butanol/glacial acetic acid/water (4:1:1), visualisation with ultraviolet light].

EXAMPLE 4

Preparation of the sodium salt of (7R)-7-[2-(2-furyl)-2-(methoxyimino)acetamido]-3-[[(1,4,5,6-tetrahydro-4methyl-5,6-dioxo-as-triazin-3-yl)thio]methyl]-3-cephem-4-carboxylic acid.

This salt is prepared in a manner analogous to that described in Example 1 from 3.4 g of 2-methoxyimino-2-furyl-acetic acid (syn/anti mixture 80:20) and 7.46 g of (7R)-7-amino-3-desacetoxy-3-[(1,4,5,6-tetrahydro-4-methyl-5,6-dioxo-as-triazin-3-yl)thio]cephalosporanic acid. The product is a beige powder (syn/anti mixture 80:20); $[\alpha]_D^{20} = -44°$ (c=0.5 in water); $R_f$ value=0.34 [thin-layer chromatography on Kieselgel-$F_{254}$-finished plates in butanol/glacial acetic acid/water (4:1:1), visualisation with ultraviolet light].

EXAMPLE 5

Preparation of the sodium salt of (7R)-7-[2-(methoxyimino)-2-(2-thienyl)acetamido]-3-[[(1,2,5,6-tetrahydro-2-methyl-5,6-dioxo-as-triazin-3-yl)thio]methyl]-3-cephem-4-carboxylic acid This salt is prepared in a manner analogous to that described in Example 1 from 1.85 g of 2-methoxyimino-2-thienyl-acetic acid (syn/anti mixture ca 70:30) and 3.71 g of (7R)-7-amino-3-desacetoxy-3-[(1,2,5,6-tetrahydro-2-methyl-5,6-dioxo-as-triazin-3-yl)thio]-cephalosporanic acid. The product is a beige powder (syn/anti mixture ca 70:30); $[\alpha]_D^{20} = -128.2°$ (c=0.5 in water); $R_f$ value=0.21 [thin-layer chromatography on Kieselgel-$F_{254}$-finished plates in butanol/glacial acetic acid/water (4:1:1), visualisation with ultraviolet light].

EXAMPLE 6

Preparation of the disodium salt of (7R)-7-[2-(2-furyl)-2-(methoxyimino)acetamido]-3-[[(2,5-dihydro-2-methyl-5-oxo-6-hydroxy-as-triazin-3-yl)thio]methyl]-3-cephem-4-carboxylic acid This salt is prepared in a manner analogous to that described in Example 1 from 10.12 g of 2-methoxyimino-2-furyl-acetic acid (syn isomer) and 18.7 g of (7R)-7-amino-3-desacetoxy-3-[(1,2,5,6-tetrahydro-2-methyl-5,6-dioxo-as-triazin-3-yl)thio]-cephalosporanic acid. For the salt-formation there are used 20 ml (2 equivalents) of a 2-N solution of sodium 2-ethylcaproate in ethyl acetate. The product is an almost colourless powder (syn isomer); $[\alpha]_D^{20}= -141.6°$ (c=0.5 in water); $R_f$ value =0.14 [thin-layer chromatography on Kieselgel-$F_{254}$-finished plates in butanol/glacial acetic acid/water (4:1:1), visualisation with ultraviolet light].

EXAMPLE 7

Preparation of the sodium salt of (7R)-3-[[(1-ethyl-1,4,5,6-tetrahydro-5,6-dioxo-as-triazin-3-yl)thio]methyl]-7-[2-(2-furyl)-2-(methoxyimino)acetamido]-3-cephem-4-carboxylic acid This salt is prepared in a manner analogous to that described in Example 1 from 1.69 g of 2-methoxyimino-2-furyl-acetic acid (syn isomer) and 3.85 g of (7R)-7-amino-3-desacetoxy-3-[(1-ethyl-1,4,5,6-tetrahydro-5,6- dioxo-as-triazin-3-yl)thio]-cephalosporanic acid. The product is a beige powder (syn/anti mixture ca 70:30); $[\alpha]_D^{20} = -47.2°$ (c=0.5 in water); $R_f$ value=B 0.47 [thin-layer chromatography on Kieselgel-$F_{254}$-finished plates in butanol/glacial acetic acid/water (4:1:1), visualisation with ultraviolet light].

EXAMPLE 8

Preparation of the sodium salt of (7R)-7-[2-[(carbamoylmethoxy)imino]-2-(2-furyl)acetamido]-3-[[(1,4,5,6-tetrahydro-4-methyl-5,6-dioxo-as-triazin-3-yl)thio]methyl]-3-cephem-4-carboxylic acid 9.76 g of [α-[(carbamoylmethoxy)imino]furfuryl]-cephalosporin sodium salt (syn/anti mixture ca 70:30) are suspended together with 4.77 g of 1,4,5,6-tetrahydro-4-methyl-5,6-dioxo-3-mercapto-as-triazine in 200 ml of phosphate buffer having a pH of 6.4. The pH is adjusted to 6.4 using 1-N sodium hydroxide while gassing with nitrogen, whereby a dark solution is obtained. This solution is stirred at pH 6.4–6.5 for 6 hours at 55°–60° C. while gassing with nitrogen, the pH being held constant with the aid of an autotitrator with the addition of 1-N sodium hydroxide. The solution is cooled to 0°–5° C. and the pH is adjusted to 2 with 2-N hydrochloric acid, whereby the product separates out as the acid. This is filtered off under suction, washed with ice/water and dried at 40° C. overnight in vacuo. The product is obtained in the form of the crude acid. For purification, this crude acid is dissolved in 150 ml of methanol and the solution is boiled with active carbon for 2 minutes. The mixture is filtered through a fluted filter and the orange coloured filtrate is concentrated in vacuo. The resin which thereby precipitates is separated and rejected. The concentrated methanolic solution is poured into ether. The acid which thereby precipitates is filtered off under suction and washed with ether and with low-boiling petroleum ether. The product is obtained in the form of the pure acid which, for conversion into the sodium salt, is dissolved in 100 ml of methanol and treated with 5 ml of a 2-N solution of sodium 2-ethylcaproate in ethyl acetate. A small amount of insolubles is filtered off and the orange coloured filtrate is concentrated at 40° C. in vacuo. This concentrated solution is added to ethanol, whereby the sodium salt precipitates. This salt is filtered off under suction, washed with ethanol and low-boiling petroleum ether and dried at 40° C. overnight in vacuo. There is obtained the sodium salt of (7R)-7-[2-[(carbamoylmethoxy)-imino]-2-(2-furyl)acetamido]-3-[[(1,4,5,6-tetrahydro-4-methyl-5,6-dioxo-as-triazin-3-yl)thio]methyl]-3-cephem-4-carboxylic acid in the form of a beige powder (syn/anti mixture ca 70:30); $[\alpha]_D^{20} = -30.1°$ (c=1 in water); $R_f$ value =0.29 [thin-layer chromatography on Kieselgel-$F_{254}$-finished plates in butanol/glacial acetic acid/water (4:1:1), visualisation with ultraviolet light].

When the starting materials used in the preceding paragraph are replaced by equivalent amounts of [α-[(methoxy)-imino]furfuryl]cephalosporin and 1,2,5,6-tetrahydro-2-methyl-5,6-dioxo-3-mercapto-as-triazine, then there is obtained under otherwise similar conditions the sodium salt of (7R)-7-[2-(2-furyl)-2-(methoxyimino)acetamido]-3-[[(1,2,5,6-tetrahydro-2-methyl-5,6-dioxo-as-triazin-3-yl)thio]methyl]-3-cephem-4-carboxylic acid. This salt is identical with the salt obtained according to Example 1.

The following Example illustrates the preparation of a pharmaceutical preparation provided by the present invention:

EXAMPLE A

Preparation of dry ampoules for intramuscular administration

A lyophilisate of 1 g of the sodium salt of (7R)-7-[2-(2-furyl)-2-methoxyimino)acetamido]-3-[[(1,2,5,6-tetrahydro-2-methyl-5,6-dioxo-as-triazin-3-yl)thio]methyl]-3-cephem-carboxylic acid is prepared in the usual manner and filled into an ampoule. Prior to the administration, the latter is treated with 2.5 ml of a 2% aqueous lidocaine hydrochloride solution.

What is claimed:

1. A compound of the formula

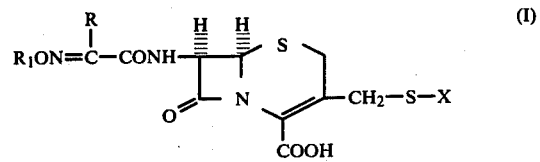

wherein R represents furyl, thienyl phenyl or phenyl substituted by a member of the group consisting of halogen, hydroxy, lower alkoxy or lower alkyl, $R_1$ represents lower alkyl or aminocarbonylmethyl and X represents a group of the formula

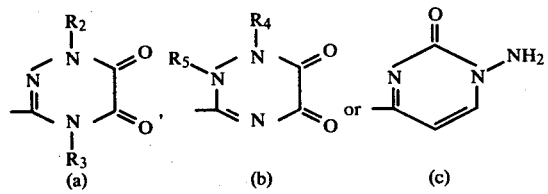

in which one of the two symbols $R_2$ and $R_3$ or $R_4$ and $R_5$ represents hydrogen and the other represents lower alkyl, carboxymethyl or sulphomethyl, and the pharmaceutically acceptable salts of said compounds and hydrates of said salts.

2. A compound as in claim 1, wherein R represents furyl and the pharmaceutically acceptable salts of said compound and hydrates of said salts.

3. A compound as in claim 2, wherein $R_1$ represents methyl, and the pharmaceutically acceptable salts of said compounds and hydrates of said salts.

4. A compound as in claim 3, wherein X represents the group of formula (c) or a group of formula (a) or (b) in which one of the two symbols $R_2$ and $R_3$ or $R_4$ and $R_5$ represents hydrogen and the other represents methyl, and the pharmaceutically acceptable salts of said compound and hydrates of said salts.

5. A compound as in claim 4, wherein X represents the 1,2,5,6-tetrahydro-2-methyl-5,6-dioxo-as-triazin-3-yl group.

6. A compound as in claim 4, wherein X represents the 1,4,5,6-tetrahydro-4-methyl-5,6-dioxo-as-triazin-3-yl group.

7. The compound: (7R)-7-[2-(2-Furyl)-2-(methoxyimino)acetamido]-3-[[(1,2,5,6-tetrahydro-2-methyl-5,6-dioxo-as-triazin-3-yl)thiolmethyl]-3-cephem-4-carboxylic acid and the pharmaceutically acceptable salts of the compound and hydrates of said salts.

* * * * *